United States Patent [19]

Harris, Jr.

[11] Patent Number: 4,558,820
[45] Date of Patent: Dec. 17, 1985

[54] VAPOR-DISPENSING DEVICE

[75] Inventor: William C. Harris, Jr., Racine County, Wis.

[73] Assignee: S. C. Johnson & Son, Inc., Racine, Wis.

[21] Appl. No.: 488,288

[22] Filed: Apr. 25, 1983

[51] Int. Cl.⁴ .............................................. A61L 9/04
[52] U.S. Cl. ......................................... 239/56; 239/57
[58] Field of Search ....................... 239/53, 55, 56, 57, 239/54, 58, 59, 309

[56] References Cited

U.S. PATENT DOCUMENTS

| | | | |
|---|---|---|---|
| 3,343,664 | 9/1967 | Poitras | 239/57 X |
| 3,727,840 | 4/1973 | Nigro | 239/43 |
| 3,858,807 | 1/1975 | Rabussier et al. | 239/57 X |
| 4,130,245 | 12/1978 | Bryson | 239/56 X |
| 4,161,284 | 7/1979 | Rattan | 239/43 |

FOREIGN PATENT DOCUMENTS 765280 4/1971 Belgium ............................... 239/57

Primary Examiner—Andres Kashnikow
Assistant Examiner—Daniel R. Edelbrock

[57] ABSTRACT

A device for dispensing air-treating vapors having a frame, two relatively movable support members mounted in the frame, having facing, substantially parallel support surfaces and being relatively movable within the frame to adjust the spacing between the surfaces, and a flexible, generally flat dispensing pouch sandwiched between the support surfaces and having an inner storage container of flowable air-treating composition which is burstable by sandwiching pressure exerted through the support surfaces to release the composition for dispensing through apertures in the support members. The support surfaces squeeze and support the dispensing pouch to hold the released composition in contact with a good part of the inner surface of the dispensing pouch.

7 Claims, 4 Drawing Figures

U.S. Patent  Dec. 17, 1985  4,558,820
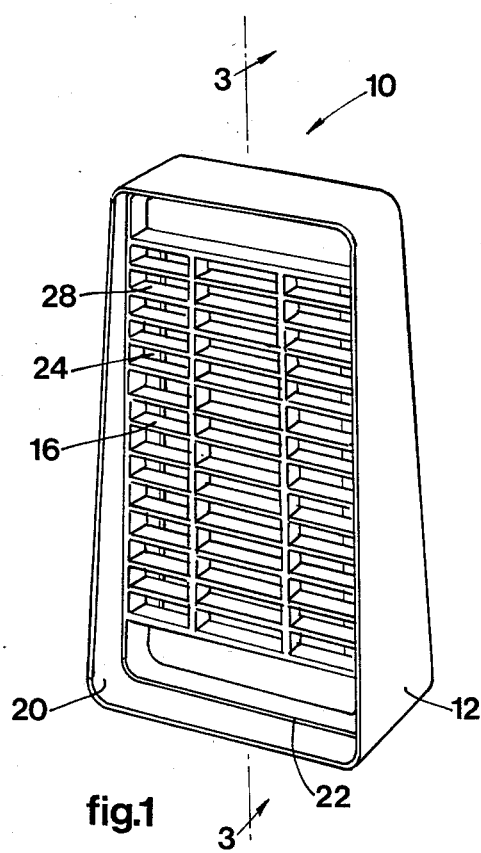
fig.1
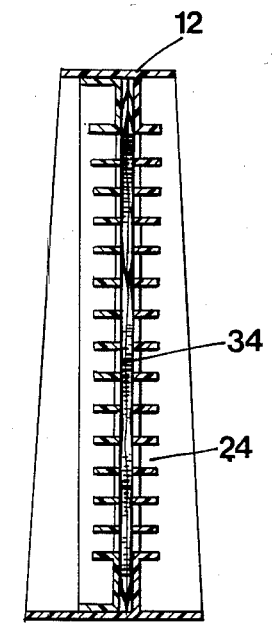
fig.3   fig.4
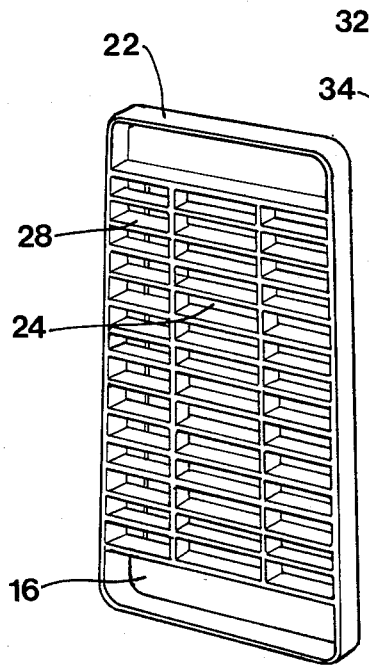
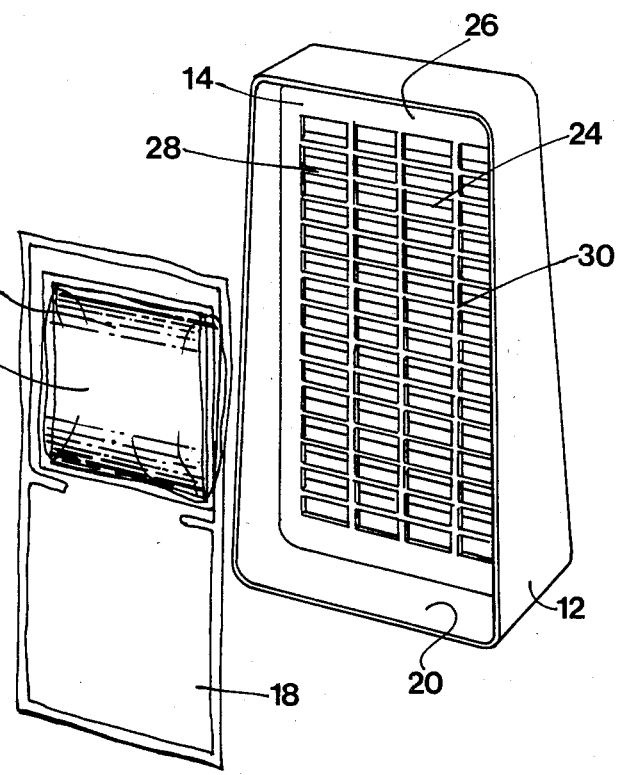
fig.2

VAPOR-DISPENSING DEVICE

FIELD OF THE INVENTION

This invention relates to devices for providing a continuous release of air-treating vapors. More specifically, this invention relates to devices for releasing vapor to the atmosphere at a substantially constant rate.

BACKGROUND OF THE INVENTION

A great variety of devices have been developed to dispense air-treating vapors. A number of the recent inventions in this field include a liquid air-treating composition in an enclosure all or part of which is formed of a polymeric material (such as film) through which the air-treating composition can migrate to be released as a vapor at an outer surface. Use of such a permeable polymeric material controls the dispensing of air-treating vapors and tends to eliminate great variations in the rate of dispensing over the life of the product. Such products are considered advantageous in this regard when compared with the many air-treating products for which the rate of vapor release drops dramatically over the life of the product.

When such enclosures are in the form of flexible plastic bags containing liquid or other flowable material, as disclosed, for example, in PCT Publications No. WO 82/02700, the rate of vapor-dispensing will vary as the area of contact between the contained liquid and the inner surface of its enclosure varies. Pooling of the liquid at the enclosure bottom, as can often occur depending on the orientation of the enclosure, can substantially reduce the dispensing rate. The rate of vapor-dispensing is significantly increased and will remain very steady over the life of the product when the liquid is in contact with all or nearly all of the inner surface of the enclosure.

This problem is specifically pointed out in U.S. Pat. No. 4,130,245 (Bryson), entitled "Liquid Dispensing Package." See, for example, column 1, lines 23–40. The Bryson patent attempts to solve this problem by dividing the flexible plastic bag into a plurality of small chambers such that the liquid will not pool primarily in one location. While this approach may have some advantages for certain types of packages, it cannot readily be used when the flexible dispensing bag is of the type having a single chamber which encloses a smaller burstable inner storage container filled with an air-treating liquid composition to be released into the flexible dispensing bag upon bursting, as is shown in FIG. 1 of PCT Publication No. WO 82/02700.

The Bryson invention is not applicable to the problem of uneven dispensing for flexible dispensing bags of the type shown herein. There is a need for a device to improve the distribution of a liquid air-treating composition within a flexible enclosure of the type having a single dispensing chamber, in order that the full advantages of dispensing by permeation through polymeric materials can be realized.

There is a need for an improved device for supporting a flexible plastic pouch for dispensing air-treating vapors from a contained liquid. Such improved device should serve to isolate the pouch away from finished furniture surfaces which would be attacked by the dispensed composition, and also to eliminate the need for human contact with such pouch while allowing good air circulation against the pouch and easy visual inspection to determine when the pouch is empty.

DESCRIPTION OF THE INVENTION

The present invention is a device for dispensing air-treating vapors from a flexible, generally flat dispenser pouch containing a liquid air-treating composition. The device of this invention overcomes the problems of prior art devices while providing the other desirable functional qualities mentioned above.

The device of this invention includes a frame, which may be adapted to rest on a table top or other surface or to hang or be otherwise supported. Two support members are mounted across the frame such that a flexible, generally flat dispensing pouch can be supported between them. The support members have facing, substantially parallel support surfaces (one surface on each of the support members) and are relatively movable within the frame to adjust the spacing of such surfaces. At least one, and preferably both, of the support members are apertured to allow access of the atmosphere to the outer surfaces of the flexible dispensing pouch. The flexible pouch is sandwiched between the support surfaces and can be squeezed by sandwiching force exerted through the support members.

The flexible dispenser pouch includes an inner storage container filled with a flowable, vaporizable air-treating composition, preferably a liquid. Such inner storage container is burstable by sandwiching pressure exerted through the support surfaces to release the composition into the flexible dispenser pouch for dispensing by permeation through the surface of the pouch.

In preferred embodiments, one of the support members is in fixed position with respect to the frame, most preferably integrally formed with the frame; and the other support member is frictionally held and slidably movable within the frame to adjust the spacing of the support surface. In preferred embodiments, each apertured support member has a multiplicity of grill members arranged such that their edges are co-planar and form at least part of the support surface of such apertured support member. The grill members are closely spaced to provide adequate bursting and support engagement with the flexible dispenser.

OBJECTS OF THE INVENTION

It is an object of this invention to provide a device for dispensing air-treating vapors overcoming problems of the prior art.

Another object of this invention is to provide an improved air-treating vapor dispenser of the type including a liquid air-treating composition within a flexible enclosure.

Another object of this invention is to provide a dispenser for air-treating vapors of the type described which minimizes variations in the rate of vapor-dispensing over the life of the product.

These and other important objects of the invention will be apparent from the following description of preferred embodiments of the invention and from the accompanying drawings wherein:

BRIEF DESCRIPTION OF THE DRAWINGS

FIG. 1 is a perspective view of the device of this invention.

FIG. 2 is an exploded perspective view.

FIG. 3 is a side sectional view as indicated in FIG. 1, showing the device before bursting of the inner storage container.

FIG. 4 is another side sectional view showing the device after bursting of the inner storage container.

DETAILED DESCRIPTION OF PREFERRED EMBODIMENTS

The drawings illustrate a preferred vapor-dispensing device 10 in accordance with this invention. Vapor-dispensing device 10 includes a frame 12, a first support member 14 which is integrally formed with frame 12, a second support member 16 which is frictionally held and slidably movable within frame 12, and a flexible, generally flat vapor-dispensing pouch 18 sandwiched between first and second support members 14 and 16.

Frame 12 has an inner surface 20 which frictionally engages the outer surface 22 of second support member 16, and holds it at whatever position it has been placed within frame 12. First support member 14 and second support member 16 each define a number of apertures 24. Each support member has a generally upright support surface 26. The support surfaces 26 face each other and are parallel, and vapor-dispensing pouch 18 is sandwiched between them.

Support members 14 and 16 each have a multiplicity of grill members 28. The grill members 28 of each support member have co-planar edges 30 which form at least part of the support surface 26. The apertures 24 between grill members 28 are generally small in size, grill members 28 of each support member being spaced closely enough to provide adequate support engagement with vapor-dispensing pouch 18. If the apertures 24 are too large, portions of flexible vapor-dispensing pouch 18 will be received within such apertures, and it will be more difficult to support the lateral surfaces of pouch 18 in a generally flat condition.

Within an upper portion of vapor-dispensing pouch 18 is an inner storage container 32 which holds a liquid air-treating composition 34 before the device is activated for use. Inner storage container 32 is itself a flexible plastic pouch, formed of material which is impermeable to the liquid composition 34. Vapor-dispensing pouch 18 is made of a permeable plastic material through which liquid composition 34 can migrate to be released at its outer surface as a vapor. Suitable materials for pouch 18 and pouch 32 are known in the art and do not form part of this invention. However, attention is directed to the above-mentioned PCT International Publication and to U.S. Pat. Nos. 3,951,622 and 4,248,380, which discuss materials and liquid compositions which are suitable for use in this invention. Particular attention is directed to a commonly assigned patent application of Edward J. Malek, entitled "Method for Forming a Burstable Pouch," Ser. No. 586,452, filed Mar. 5, 1984, which is a continuation-in-part of Ser. No. 488,287, filed simultaneously with this application on Apr. 25, 1983, now abandoned.

When it is desired to activate vapor-dispensing device 10, the user squeezes first and second support members 14 and 16 together until inner storage container 32 bursts, releasing air-treating liquid 34 into the remaining portion of vapor-dispensing pouch 18. Support members 14 and 16 can be squeezed together until liquid 34 is distributed across vapor-dispensing pouch 18 to give complete or nearly complete contact of liquid 34 with the lateral walls of pouch 18, as illustrated in FIG. 4. During such squeezing movement, second support member 16 will move with respect to frame 12 and first support member 14. Second support member 16 will then stay in place by virtue of its frictional engagement within frame 12.

Vapor-dispensing pouch 18 is preferably translucent and, most preferably, both pouch 18 and pouch 32 are translucent. This enables the user to determine when the liquid composition has been fully dispensed. Varying degrees of translucency are possible; indeed, the pouches can be transparent or nearly transparent. It is only desirable that the user be able to see the contents of such pouches.

The grill members 28 and apertures 24 may be made in a variety of shapes and sizes. This invention lends itself to considerable decorative variety.

Frame 12 and the first and second support members 14 and 16 are preferably made of plastic materials such as high density polyethylene, polypropylene, nylons, or any of a variety of suitable materials.

While in the foregoing specification, this invention has been described in relation to certain preferred embodiments and many details have been set forth for purpose of illustration, it will be apparent to those skilled in the art that the invention is susceptible to additional embodiments and that certain of the details decribed herein can be varied considerably without departing from the basic principles of the invention.

What is claimed is:

1. A device for dispensing air-treating vapors comprising:

a frame having an inner peripheral surface;

first and second support members mounted across the frame, said support members having facing, substantially parallel, non-deformable planar support surfaces, at least one of such support members having an outer peripheral surface mating frictionally with said inner surface and being slidable linearly along said inner frame surface to adjust the spacing between such surfaces and at least one of such support surfaces being apertured;

a flexible, generally flat dispenser sandwiched between the support surfaces and having an inner storage container of vaporizable air-treating composition which is burstable by sandwiching pressure exerted manually through the support surfaces by said relative movement to release the composition for dispensing;

said slidable support member engaging said peripheral surface of said frame with sufficient frictional force to maintain said support surfaces in such reduced spacing without continued manual pressure to hold said flexible dispenser tightly therebetween.

2. The device of claim 1 wherein one of said support members and said frame are integrally formed.

3. The device of claim 1 wherein both support surfaces are apertured.

4. The device of claim 3 wherein each apertured support member has a multiplicity of grill members arranged to have co-planar edges forming at least part of its support surface, the grill members being closely spaced for adequate bursting and supporting engagement with the dispenser.

5. The device of claim 1 wherein the dispenser comprises a sealed outer pouch formed of material through which the air-treating composition can permeate and, as the inner storage container, an inner pouch formed of material impermeable to the composition.

6. The device of claim 5 wherein both support surfaces are apertured.

7. The device of claim 6 wherein each apertured support member has a multiplicity of grill members arranged to have co-planar edges forming at least part of its support surface, the grill members being closely spaced for adequate bursting and supporting engagement with the dispenser.

* * * * *